United States Patent [19]
Ashburn

[11] Patent Number: 6,147,352
[45] Date of Patent: Nov. 14, 2000

[54] LOW PROFILE OPEN RING SINGLE PHOTON EMISSION COMPUTED TOMOGRAPHIC IMAGER

[75] Inventor: William L. Ashburn, La Jolla, Calif.

[73] Assignee: Digirad Corporation, San Diego, Calif.

[21] Appl. No.: 09/028,181

[22] Filed: Feb. 23, 1998

[51] Int. Cl.[7] .................................................. G01T 1/166
[52] U.S. Cl. ................................ 250/363.05; 250/363.08
[58] Field of Search ........................ 250/363.05, 363.04, 250/363.08; 378/11

[56] References Cited

U.S. PATENT DOCUMENTS

| | | | |
|---|---|---|---|
| 4,426,578 | 1/1984 | Bradcovich et al. | 250/363 S |
| 4,503,331 | 3/1985 | Kovacs, Jr. et al. | 250/363 |
| 4,961,214 | 10/1990 | Van Endschot et al. | 378/197 |
| 5,029,192 | 7/1991 | Schwierz | 378/4 |
| 5,038,371 | 8/1991 | Janssen et al. | 378/197 |
| 5,048,069 | 9/1991 | Siczek | 378/197 |
| 5,291,540 | 3/1994 | Futamata | 378/197 |
| 5,367,554 | 11/1994 | Kobayashi et al. | 378/196 |
| 5,386,453 | 1/1995 | Harrawood et al. | 378/196 |
| 5,410,584 | 4/1995 | Schaefer et al. | 378/196 |
| 5,638,817 | 6/1997 | Morgan et al. | 128/653.1 |

FOREIGN PATENT DOCUMENTS

1589644  8/1970  Germany  .......................... 250/363.08

*Primary Examiner*—Seungsook Ham
*Assistant Examiner*—Richard Hanig
*Attorney, Agent, or Firm*—Fish & Richardson P.C.

[57] ABSTRACT

A single photon emission computer tomography (SPECT) imager for the study of a patient to whom a radionuclide has been administered. The imager has an arcuate detector carrier encompassing at least 180° of arc about an examination axis through a target area of the patient. One or more scintillation detectors are carried by the detector carrier for taking a plurality of readings of gamma ray emissions from the radionuclide. While the plurality of readings are taken, the carrier remains substantially immobile relative to the patient.

21 Claims, 10 Drawing Sheets

LOW PROFILE OPEN RING SINGLE PHOTON EMISSION COMPUTED TOMOGRAPHIC IMAGER

BACKGROUND

1. Technical Field

The present invention relates generally to medical imaging and, more particularly, to single photon emission computed tomographic (SPECT) imagers which detect gamma ray emissions from radionuclides administered to a patient.

2. Background Information

The field of medical imaging includes use of photon detectors commonly known as "gamma cameras" to detect, record, and display the uptake and distribution of radioactive drugs administered orally or intravenously to a patient. Signals generated by the gamma cameras are processed to provide a display of the internal distribution of the drugs in the patient or a particular target area or organ of the patient. The images are then interpreted by a specialist in radiology, cardiology or other relevant fields, in diagnosing any of a variety of medical conditions. Although stationary and planar gamma imaging have been used, a more advanced method is single photon emission computed tomography (SPECT) wherein a series of images or readings of gamma ray emissions are taken at regular angles around the patient, e.g., every 3 degrees about an axis through a target area or organ (such as the heart). The resulting images or data are processed using standard "back-projection" computer algorithms to construct one or more cross-sectional (tomographic) views of the body, target area, or organ. These images may be displayed as a single slice, a stack of slices oriented orthogonal to the axis or by other appropriate means. In the case of cardiac SPECT, the tomographic images are displayed as slices orthogonal to the long axis of the left ventricle.

SPECT has an advantage over conventional planar imaging of achieving greater contrast between normal and abnormal radioisotope uptake. In the diagnosis of coronary artery heart disease, increased image contrast is important to more clearly identify zones of the heart muscle (myocardium) which may be injured (infarcted) or may be at risk for subsequent ischemic injury.

Such conditions may warrant emergency admission to the hospital for more intensive observation or therapeutic intervention such as administration of anti-clotting drugs, cardiac catheterization or more radical surgery. Radionuclide SPECT has thus become a standard technique used in the diagnosis and prognosis of heart disease as well as disorders of the brain and other organs.

It is known that cardiac SPECT can be performed by rotating the gamma camera detector head through only 180 degrees rather than through a full 360 degrees. In this case, the imaging detector acquires data while it rotates through 180 degrees over the front of the chest. Because of the normal location of the heart, data recording begins with the detector head in the 45 degree right-anterior-oblique (RAO) position, which is slightly in front of the right shoulder, and ends in left-posterior-oblique (LPO) position, which is slightly behind the left shoulder.

Accordingly, manufacturers of commercial gamma cameras allow rotation of their detector heads either through 180 or 360 degrees. In addition, some manufacturers offer the choice of rotations that use an elliptical rather than circular path or orbit. In theory, an elliptical orbit allows the detector to travel in an orbit more closely corresponding to the elongate cross-section of the human torso. Accordingly, the imager head is closer to the patient's heart at all times, and provides better image quality. Additionally, some manufacturers offer the option of a continuous mode of data recording during rotation rather than the more usual "step-and-shoot" method of obtaining individual images at approximately 3 degree intervals through 180 or 360 degrees. The continuous mode reduces acquisition time, which may be important in studying very ill patients in an emergency setting.

As an alternative to rotating the gamma camera detector head around the patient, as used in conventional SPECT imaging, Kan et al., published a report in the Journal of Nuclear Medicine in the late 1970's in which they demonstrated that the detector could remain stationary while the patient was turned in a chair in front of the camera. This "rotating chair" method is currently embodied in a gamma camera manufactured by Picker International (formerly known as the Sinticor model SIM 400 Multi-crystal Camera). While rotating chair tomography may be useful with a reasonably healthy and cooperative patient, it is difficult with an acutely ill individual who must raise and maintain his or her left arm in a position above the chest and away from the heart. In patients confined to a bed this technique is unsuitable.

There are several gamma camera designs that utilize a single ring or multiple contiguous rings of radiation detectors. However, these imaging cameras are generally intended for brain SPECT and require that the patient lie on a bed or sit in a chair while the ring(s) completely surround the body or organ to be imaged. Therefore, complete ring detector configurations are impractical for SPECT imaging in an acute care setting. Furthermore, they are very heavy instruments and generally require permanent placement in a fixed location.

SPECT gamma cameras typically weigh several thousand pounds. Consequently, it is impractical to transport these imaging devices to desirable locations in the hospital such as the coronary care unit (CCU) or emergency room (ER) or department where care management decisions may depend on timely information concerning the patient's condition. One example is determining the state of myocardial perfusion in patients with unexplained chest pain, identifying risks of impending worsening of the disease and deciding if it is safe to send them home. Furthermore, because of their weight and gantry configuration, there are no known gamma cameras designed or capable of performing true SPECT imaging on patients who should remain in their existing beds, e.g., in the CCU or ER.

There are some mobile single head gamma cameras available that are capable of being transported to patient locations such as the CCU or ER. However, these instruments are not capable of performing true (multiple angle) SPECT. At best, they are capable only of performing a less useful technique called "limited angle" tomography. Examples include: "7-pinhole" and "rotating slant-angle collimator" tomography.

Consequently, the dominant method currently available to perform SPECT imaging on a patient in a CCU bed or in a similar emergency setting is to first transfer the patient to the location of the camera and place the patient on a special low attenuation bed that by design is an integral part of a gamma camera gantry assembly.

It is therefore advantageous that a SPECT imager and method be provided which allow imaging in a preexisting patient environment with little physical disturbance of the patient. Such a system would preferably accommodate multiple patient environments and orientations including supine patients in conventional hospital beds or seated patients.

SUMMARY

The present invention includes a SPECT imager for detecting gamma ray emissions from a patient to whom a radionuclide has been administered and generating images therefrom. The imager includes an arcuate detector carrier which encompasses at least 180° of arc about an examination axis through a target area of the patient to be examined. One or more detectors for sensing gamma ray emissions are carried by the detector carrier. The carrier is preferably of sufficiently low profile as to allow a portion of it to be inserted beneath the patient's mattress without undue movement or disturbance of the patient.

In one aspect the invention is directed to a method of imaging a patient to whom a radionuclide has been administered. A detector carrier member, carrying one or more detectors, is positioned about the patient so that the carrier member encompasses at least 180° of arc about an axis through a target area of the patient's body. A plurality of readings of gamma ray emissions from the radionuclide are taken at detection positions corresponding to positions of the one or more detectors along the carrier member. The carrier member remains substantially immobile relative to the patient while the plurality of readings are taken.

Implementations of the inventive method may include one or more of the following. All the detectors may be in a detector assembly which moves along the carrier member to take said plurality of readings. All the detectors may be positioned at different fixed locations along the carrier member. The positioning step may also comprise moving the carrier member so as to insert a portion of the carrier member beneath a mattress on which the patient rests, the patient passing through a gap between first and second ends of the carrier member. The moving step may comprise rotating the carrier member. The moving step may comprise translating the carrier member. The positioning step may comprise placing the carrier member around a head of the patient so that the axis is substantially parallel to an ear-to-ear axis of the patient. The positioning step may comprise placing the carrier member around the head of the patient so that the axis is substantially parallel to an axis extending from a nose of the patient to the back of the head of the patient.

In another aspect, the invention is directed to an imager for the study of a patient to whom a radionuclide has been administered. An arcuate detector carrier member encompasses at least 180 degrees of arc about an examination axis through a target area of the patient. One or more detectors are carried by the detector carrier member for taking a plurality of readings of gamma ray emissions from the radionuclide. The carrier member is substantially immobile relative to the patient while the plurality of readings are taken.

Implementations of the invention may include one or more of the following. The arc may be encompassed by the detector carrier member from a first end through a second end with sufficient gap to permit the relative ingress and egress of the patient through the gap. The detectors may be in a detector head moveable along the carrier member to take said plurality of readings. The detector head may be moveable along a circular arc defined by the carrier member. The detector head may be moveable along a non-circular arc defined by the carrier member, the noncircular arc corresponding more nearly to the perimeter of the patient than would a circular arc. The carrier member may have a shell, extending substantially along the length of the carrier member for preventing physical contact between the patient or the patient's environment and the detectors, while being substantially gamma transparent so as to allow the detectors to detect radiation passing through the shell. All the detectors may be positioned at different fixed locations along the carrier member. The carrier member may have first and second substantially flat portions, parallel to each other and joined by a curved portion, the detectors being substantially continuously arrayed along said flat portions and curved portion. A gantry may support the carrier member above a floor surface and be rotatably coupled to the carrier member for relative rotation about a horizontal axis orthogonal to the examination axis so as to accommodate multiple orientations of the examination axis. The gantry may include a base section for supporting the imager on a floor surface, a tower section extending upward from the base section, and an arm section coupling the tower section and the carrier member.

In another aspect, the invention is directed to an imager for the study of a patient. An arcuate detector carrier member encompasses an arc about an examination axis through a target area of the patient. One or more detectors are carried at least in part within the detector carrier member for taking a plurality of readings of gamma ray emissions. The carrier member is substantially immobile relative to the patient while the plurality of readings are taken. The detector carrier member may encompass less than 360° of arc about the examination axis. The carrier member may include a shell, extending substantially along the length of the carrier member for preventing physical contact between the patient and the detectors.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference numbers and designations in the various drawings indicate like elements.

DETAILED DESCRIPTION

The following description is of the best presently contemplated modes for carrying out the invention. This description is made for purpose of illustrating the general principles of the invention and should not be taken in a limiting sense. The scope of the invention is best determined by reference to the appended claims.

Figure 1:
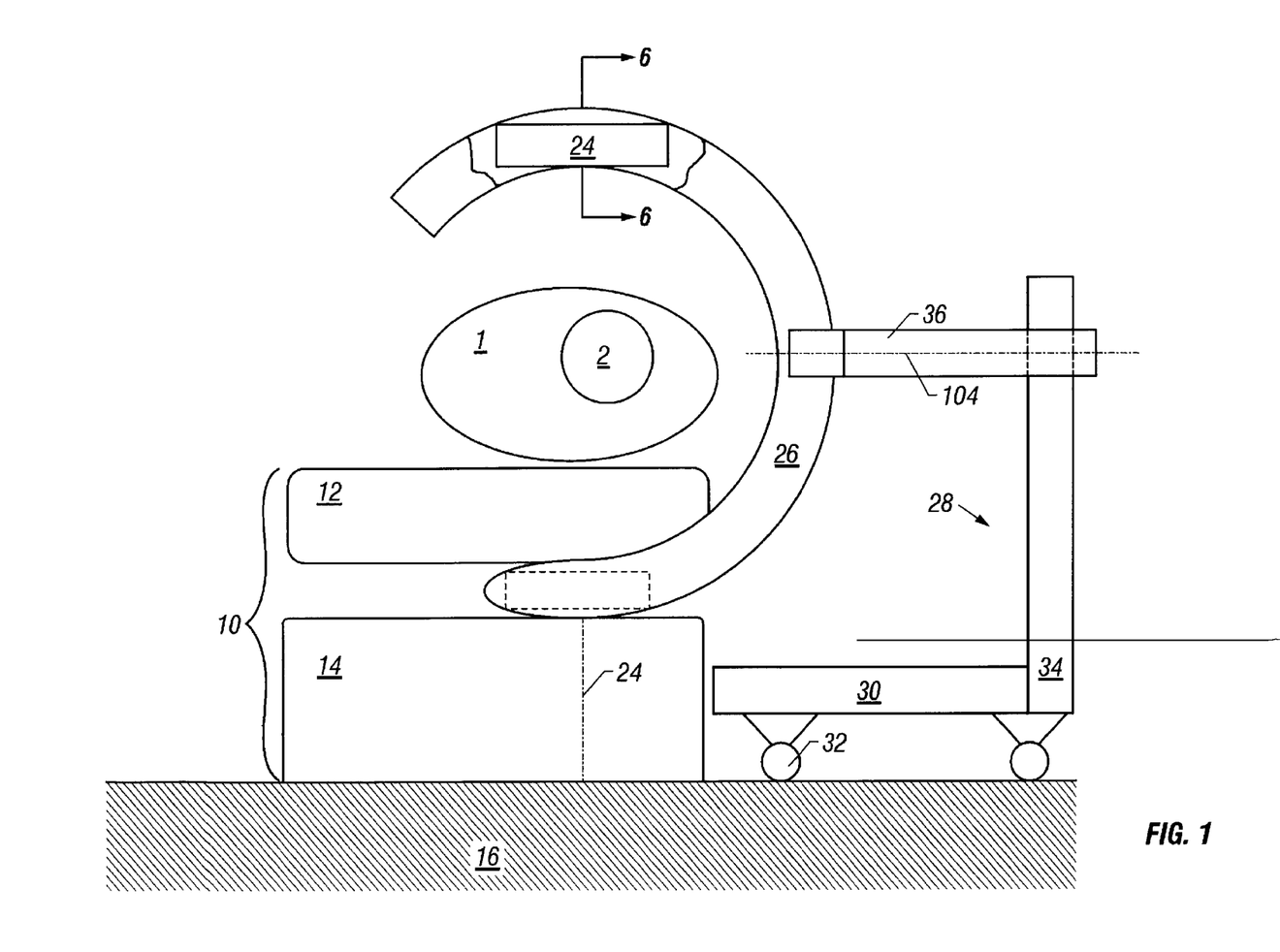
FIG. 1 is a side (axial) semi-schematic and partially cut-away view of an open ring imager according to the present invention.

As shown in FIG. 1, a patient 1 is lying in a hospital bed 10 having a mattress 12 and a supporting structure 14. The location of the patient's heart 2 is shown schematically and corresponds to a view of a supine patient from toe to head. A radionuclide drug (not shown) that preferentially concentrates in the heart is or has been administered to the patient.

A SPECT imager 20 is positioned aside the bed, adjacent the patient's left side. The imager includes a detector head 24, containing a plurality of detectors (not shown) carried by an arcuate detector carrier 26, the overall section of which is a substantially annular sector preferably of slightly greater than 180 degrees. A suitable detector head is disclosed in co-pending patent application Ser. No. 08/672,831, filed Jun. 28, 1996 now U.S. Pat. No. 5,786,597, the disclosure of which is incorporated herein by reference. The imager further includes a gantry 28 supporting the detector carrier above the floor 16. The gantry comprises a base section 30 for supporting the imager on the floor and optionally including casters 32 to facilitate movement of the imager, as well as a tower section 34 extending upward from the base and connected to a proximal end of an arm section 36, the distal end of which is connected to the carrier for holding the carrier and detector head.

Figure 2:
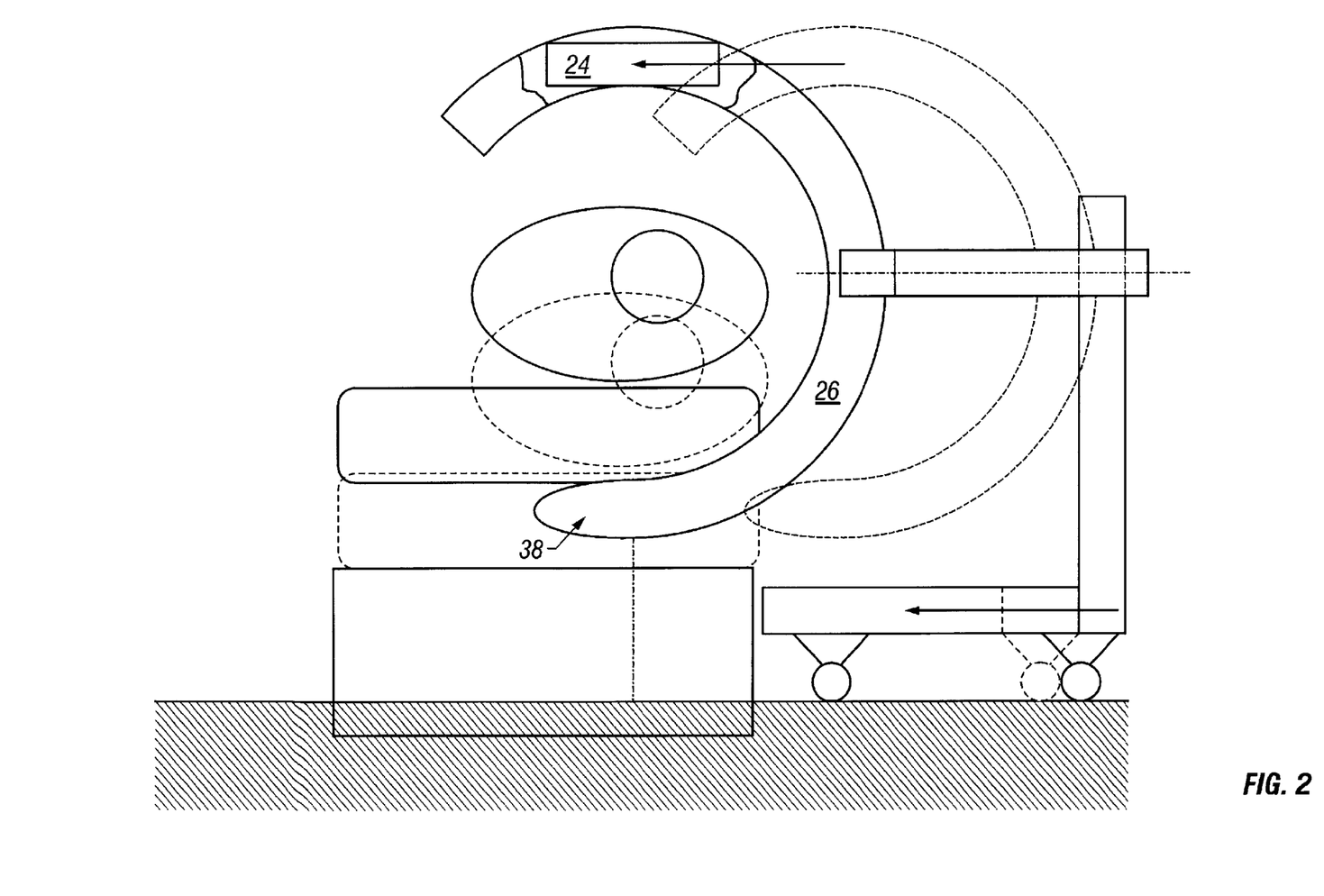
FIG. 2 is a side (axial) semi-schematic and partially cut-away view of the imager of FIG. 1 shown prior to patient ingress in broken lines and after patient ingress in solid.
Figure 3:
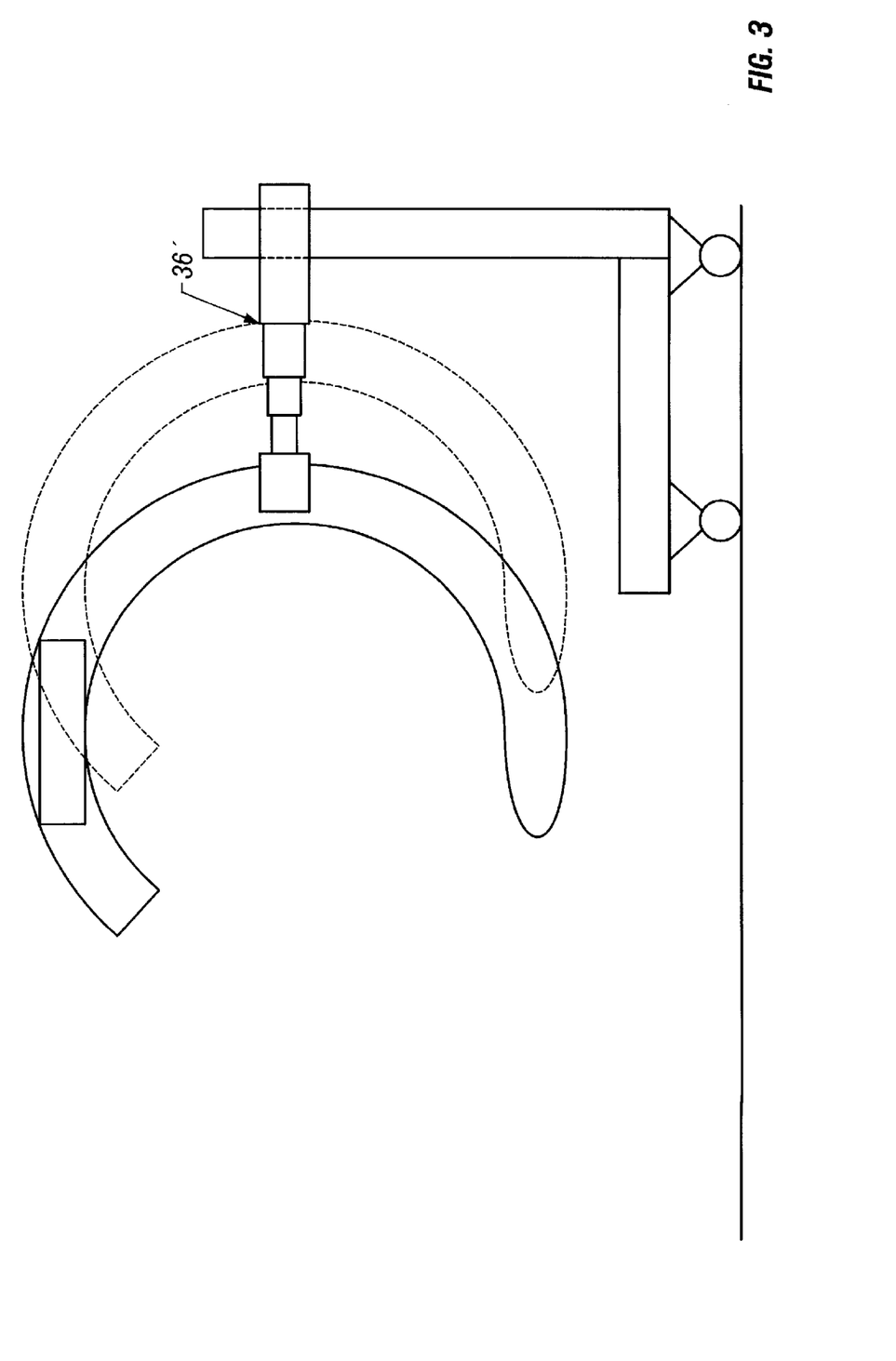
FIG. 3 is a side (axial) semi-schematic and partially cut-away view of an alternate open ring imager according to the present invention shown prior to patient ingress in broken lines and after patient ingress in solid.
Figure 4:
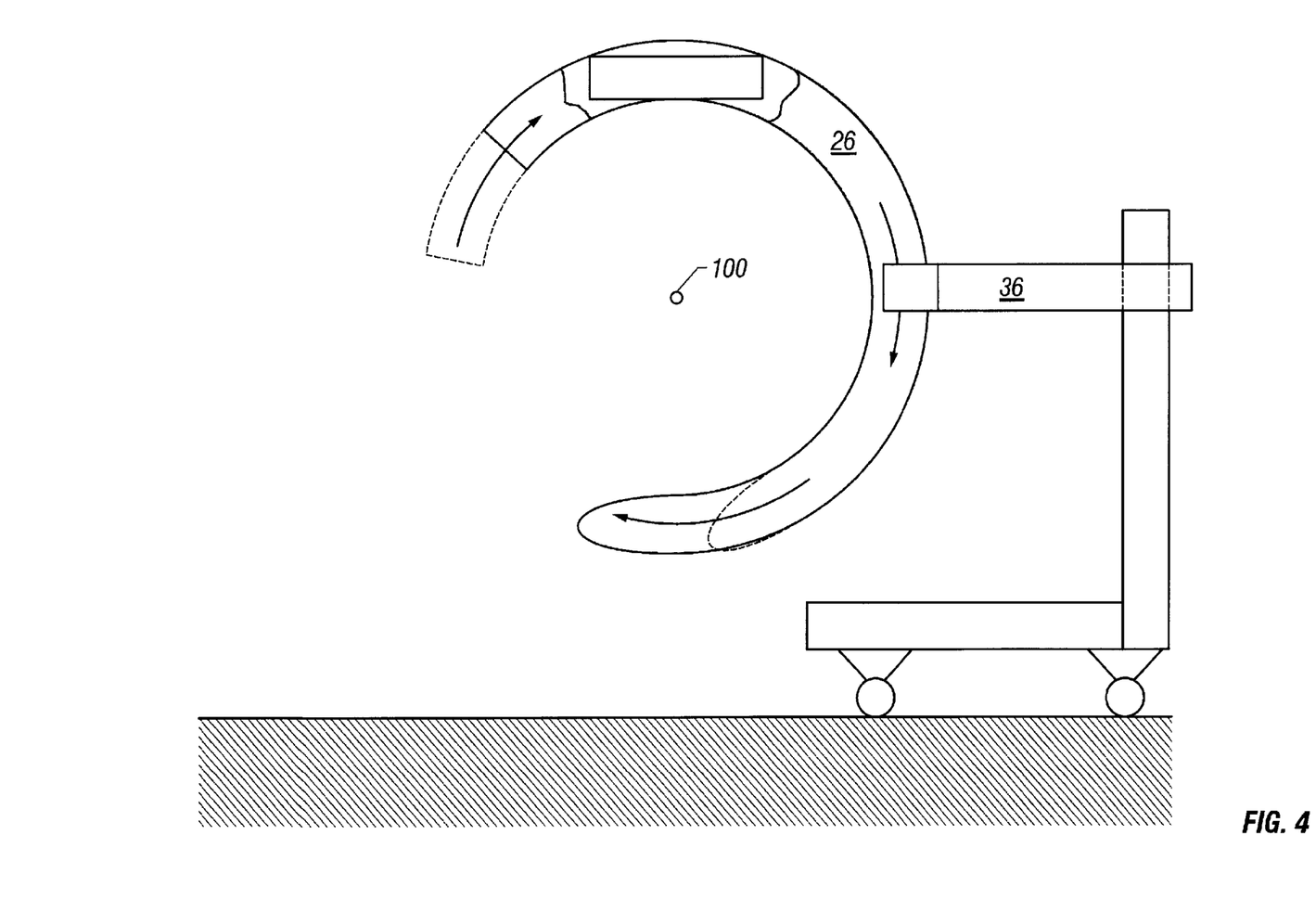
FIG. 4 is a side (axial) semi-schematic and partially cut-away view of another alternate open ring imager according to the present invention shown prior to patient ingress in broken lines and after patient ingress in solid.

As shown in FIG. 2, ingress of the patient to the imager is achieved through a gap between the upper and lower ends of the detector carrier 26. In the illustrated embodiment, the lower end 38 has a tapering contour which allows the lower portion of the carrier to be slid between the mattress and supporting structure. This may be achieved, starting with the broken line initial position, by rolling or driving the entire imager inward from the side of the bed to achieve the solid final position, or this also may be achieved via a telescoping arm 36' (FIG. 3). In addition or as an alternative to such linear translation, ingress may be achieved by a rotation of the carrier. As shown in FIG. 4, such a carrier may rotate about its central axis 100, by being driven through the distal end of the arm 36.

In the operational position, the central axis of the carrier (which defines an examination axis) is coincident with a central longitudinal axis through the patient or, more particularly, through the target organ or area of the patient's body.

As shown in FIG. 1, the detector head is movable along the carrier in a path of approximately 180° about the carrier axis. Preferably the path is slightly greater than 180° so as to provide a corresponding degree of over sampling to ensure image quality. Thus, in order to fully accommodate the detector head, the overall section of the carrier encompasses somewhat more than 180° of an arc. Initially, the detector head 24 is adjacent to the upper end of the carrier, defining a first extreme of its range of motion relative to the carrier. In the illustrated use as a cardiac SPECT imager, this is the right-anterior-oblique (RAO) position. In operation, the detector head is driven along the carrier member, taking readings either at predetermined discrete intervals, e.g., every 3°, or in a substantially continuous mode. Such operation continues until the detector head reaches a final position, shown in broken lines adjacent the lower end of the carrier and corresponding to the left-posterior-oblique (LPO) position in cardiac SPECT. Throughout this process, the carrier remains substantially immobile relative to the patient and target organ. The detector head may be driven via one or more drive motors either on the camera or the carrier. The signals from the detector head resulting from the readings of gamma ray emissions from the radionuclide as well as detector position signals from position detecting sensors (not shown) are communicated to a processing unit (not shown) where they are processed to generate images which are displayed on a conventional monitor (not shown). Egress of the patient may be achieved by simply reversing the steps involved in ingress.

Figure 5:
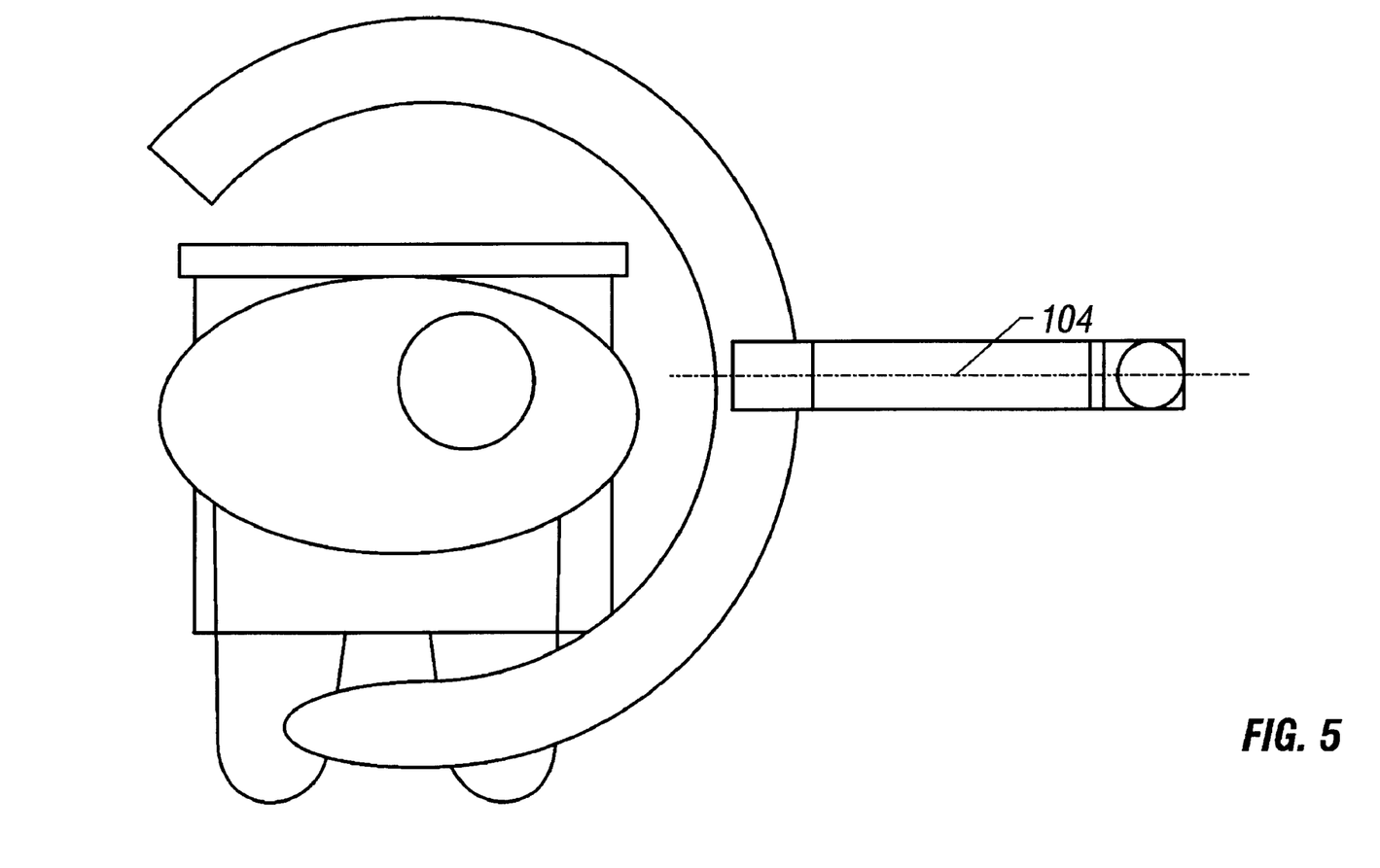
FIG. 5 is a top (axial) semi-schematic and partially cut-away view of the imager of FIG. 1, the examination axis having been rotated 90 degrees to accommodate a patient sitting in a chair.

As shown in FIG. 5, the carrier and examination axis may be rotated 90° about an axis orthogonal to the carrier axis (for example a longitudinal axis 104 of the arm) to perform SPECT on a patient seated upright in a chair. Rotation of less than 90° may, for example, be used if the patient is not fully upright but slightly reclined such as in a tilted bed or similar situation. To enhance image quality, the patient may place his or her inboard arm or both arms atop of the carrier (on the longitudinal edge of the carrier), which removes the arm(s) from the image and also allows the torso to be placed closer to the carrier (and thus to the detectors).

Figure 10:
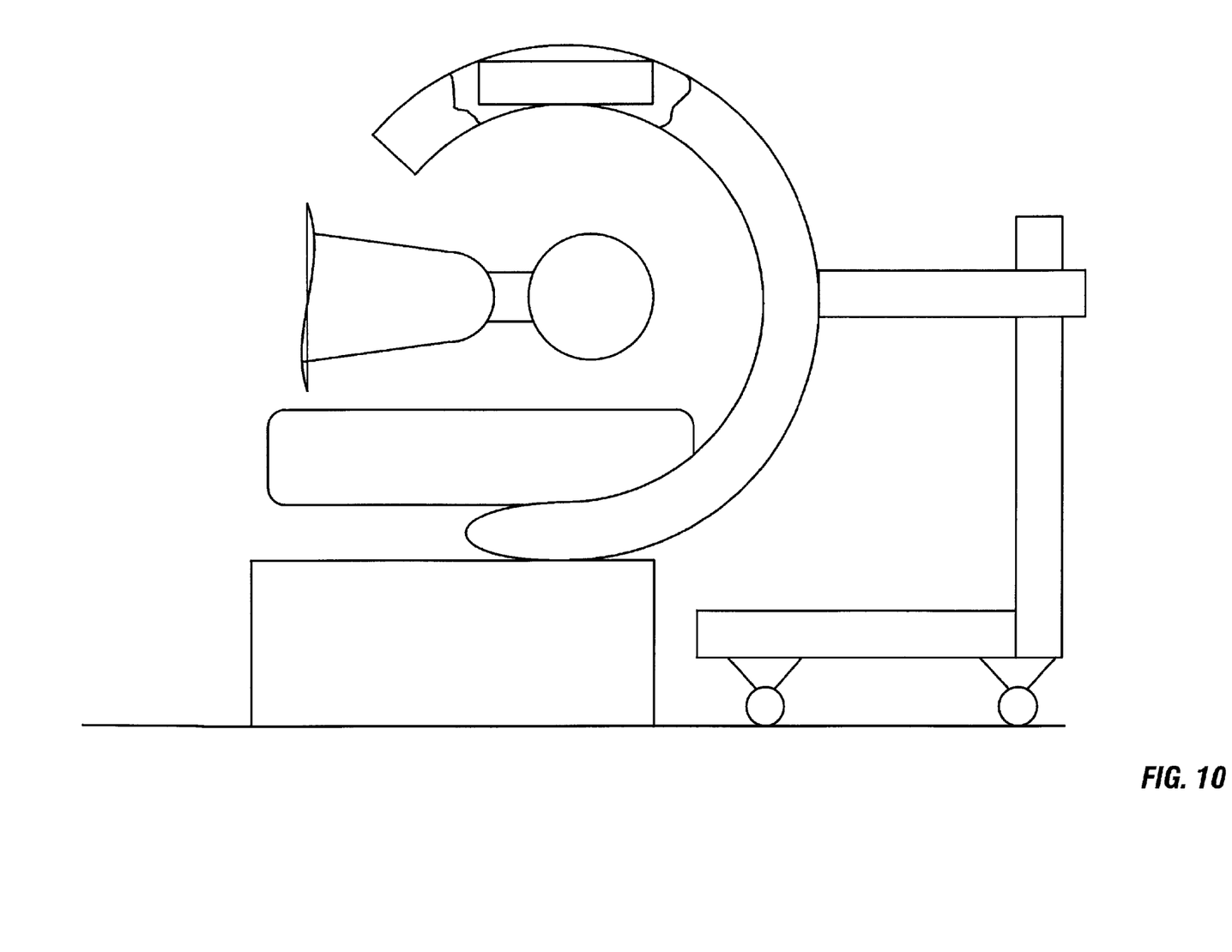
FIG. 10 is a side semi-schematic view of the imager of FIG. 1, the imager having been rotated 90° relative to the patient from the position of FIG. 1 for imaging the head of the patient.
Figure 11:
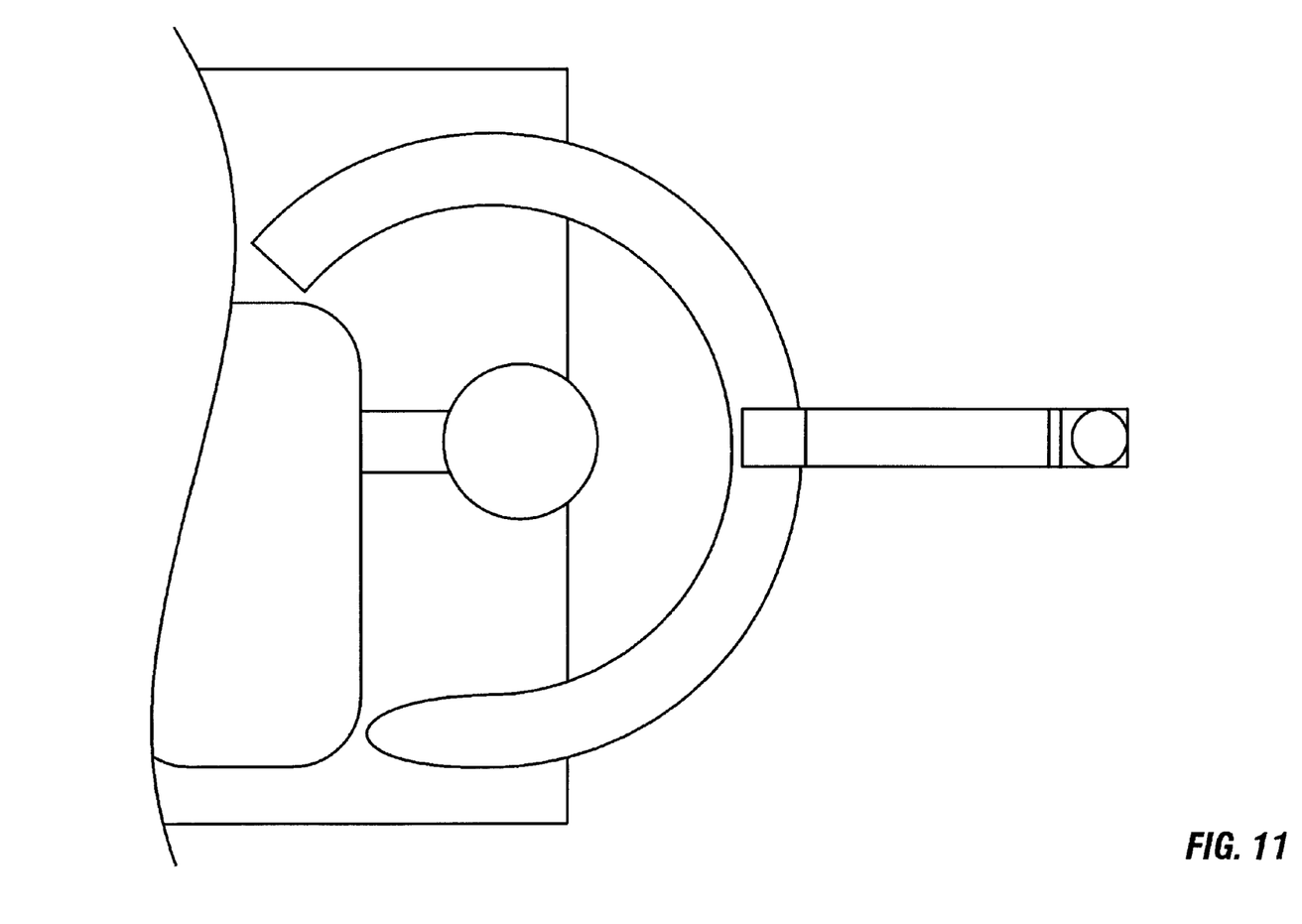
FIG. 11 is a top semi-schematic view of the imager of FIG. 1, the examination axis having been rotated 90° and the imager rotated to image the head of the patient.

Optional methods of performing SPECT on the brain include having the imager approach the bed from the head rather than the side. With the examination axis oriented transverse to the patient's head (e.g., parallel to an ear-to-ear axis) movement of the detector head provides a view from the patient's nose to the back of the patient's head (FIG. 10). An alternative is to approach from the head of the bed with the carrier in a horizontal orientation so as to provide an ear-to-ear view (FIG. 11). In such a position, the examination axis may be parallel with a front-to-back axis of the patient's head (e.g., an axis from the nose to the back of the head).

Figure 6:
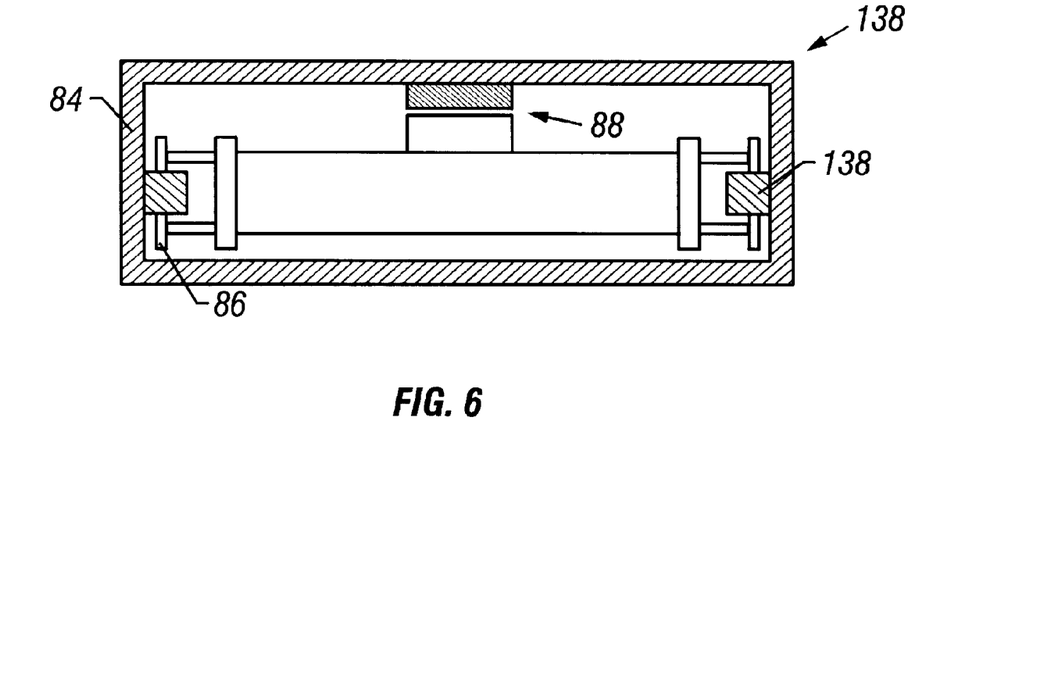
FIG. 6 is a semi-schematic sectional view through the carrier of the imager of FIG. 1 taken orthogonally to the carrier axis along line 6—6.
Figure 7:
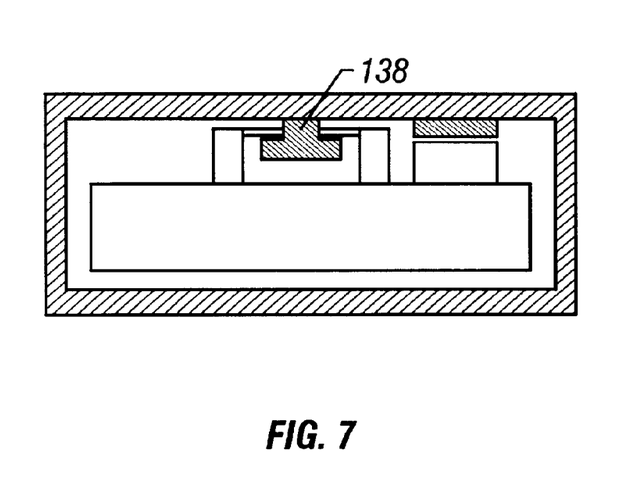
FIG. 7 is a semi-schematic sectional view of an alternate carrier mechanism.

As shown in the sectional view of FIG. 6, in one embodiment, the detector head rides between a pair of longitudinally outboard tracks 82 within the carrier. Additionally, the carrier has a shell 84 extending substantially along its length which protects the detector head and internal features of the carrier, preventing physical contact between the patient or the patient's environment (such as the bed) and the detector head. The radially inboard portion 86 of the shell is substantially gamma transparent so as to allow the detector head to detect radiation emissions from the radionuclide which must pass through the shell. To electrically couple the detector head to a processor, an annular sliding contact system 88 may be provided within the carrier member or conventional wiring or other suitable means may be used. An alternative track mechanism is shown in FIG. 7 wherein a single track 82' is located radially outboard of the detector head. This potentially provides a narrower, but thicker carrier member section than the embodiment of FIG.

6 which facilitates a low aspect ratio carrier member which is easier to insert beneath a mattress.

Figure 8:
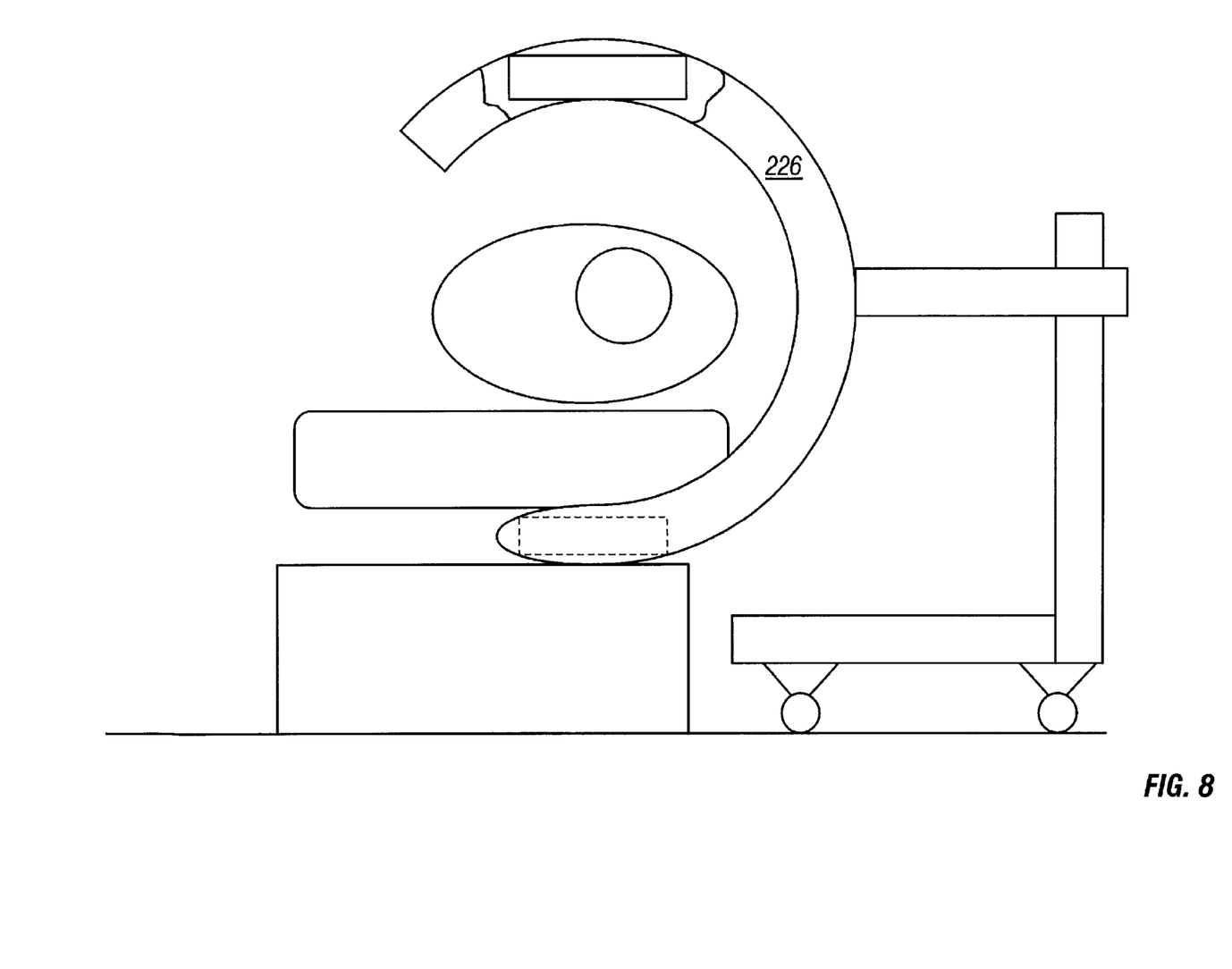
FIG. 8 is a side (axial) semi-schematic view of an open ring imager according to the present invention having a carrier of approximately elliptical section.

In the alternate embodiment of FIG. 8, the carrier 226 defines a substantially elliptical arc which corresponds more nearly to the perimeter of a patient's torso than does the circular arc.

Optional features include having the detector head be readily removable. This would facilitate both the use of a single detector head in multiple imager units (such as in the present open-ring unit and in a stationary planar imager) and the selective use of different detector heads in the single open ring imager (the detector heads being designed or tuned for different purposes such as different radiation levels, different desired image densities, or the like). In such a case, the detector head might be provided with handles which would allow it to be used as a hand-held scanner for particular purposes. With that option, electrical communication could be maintained with the processing unit by the use of extra long cabling drawn from the carrier or by separate cabling provided for such external use. Optionally a break could be made in the carrier (for example by hinging two sections of the carrier) to allow it to open yet wider to facilitate patient ingress and egress.

Figure 9:
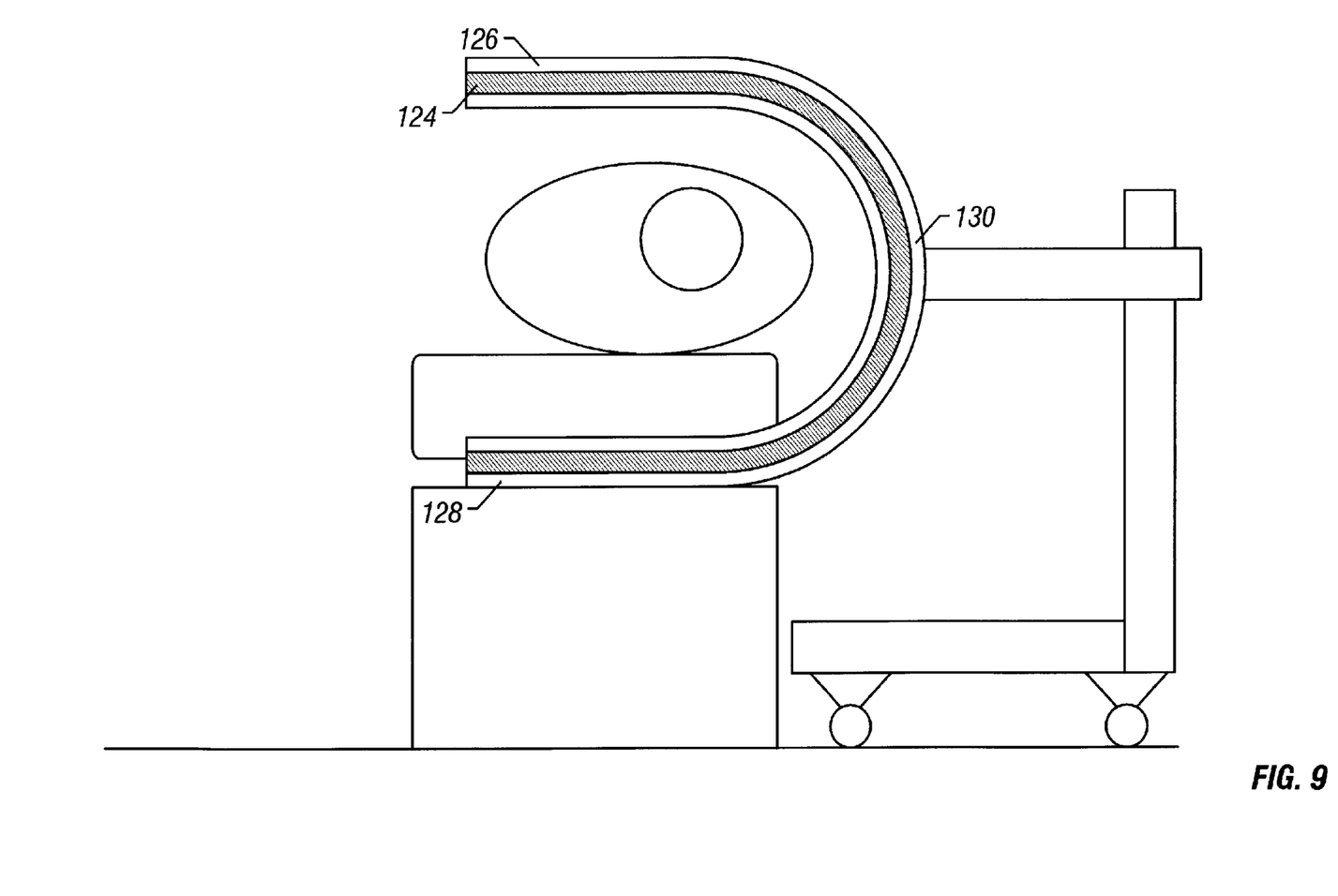
FIG. 9 is a side (axial) semi-schematic view of an open ring imager according to the present invention having fixed detectors and a carrier having flat top and bottom portions.

In yet another alternate embodiment of FIG. 9, a plurality of detectors 124 are positioned at different fixed locations along the carrier member. The resulting array of detectors extends both longitudinally and along the arc of the detector carrier and is of sufficient density to supply the desired image definition. Substantially simultaneous readings may be taken from all the detectors. The particular carrier of this embodiment is shown having upper and lower substantially flat portions 126 and 128 parallel to each other and joined by a curved portion, the detectors being substantially continuously arrayed along the flat portions and curved portions. This geometry further facilitates ingress and egress by minimizing patient disturbance when the carrier is simply translated to be inserted under the mattress. Via appropriate alignment of the detectors and programming of the processor, such noncircular and nonsimple arc profiles may be accommodated. Such profiles may also be used with a movable detector head.

Although preferred embodiments of, and/or modifications to, the present invention have been illustrated and described, it will be understood that various modifications may be made without departing from the spirit and scope of the invention. For example, various tracks or other structures may be utilized to define the detector path. Various detector head configurations may be utilized, including multipurpose detector heads or dedicated units. The shell may be fully or partially integrated with the track members such as in a monocoque structure. Further, the shell may be limited in scope to portions of the path of the detector requiring particular protection from contact with the environment. Further, but by no means finally, if desired, various other structures could be utilized to protect the detectors, such as a forked guide insertable under the mattress to hold the mattress elevated away from the detector path. Accordingly, other embodiments are within the scope of the following claims.

What is claimed is:

1. A method of imaging a patient to whom a radionuclide has been administered, comprising:

positioning a detector carrier member, carrying one or more detectors, about the patient so that the carrier member encompasses at least 180° of an arc about an axis through a target area of the patient's body; and taking a plurality of readings of gamma ray emissions from the radionuclide at detection positions corresponding to positions of the one or more detectors along the carrier member;

wherein the carrier member remains substantially immobile relative to the patient while the plurality of readings are taken;

and wherein the one or more detectors are capable of moving along the carrier member.

2. The method of claim 1, wherein all the detectors are in a detector assembly which moves along the carrier member to take said plurality of readings.

3. The method of claim 2, wherein the positioning step comprises moving the carrier member so as to insert a portion of the carrier member beneath a mattress on which the patient rests, the patient passing through a gap between first and second ends of the carrier member.

4. The method of claim 1, wherein all the detectors are positioned at different fixed locations along the carrier member.

5. The method of claim 1, wherein the positioning step comprises moving the carrier member so as to insert a portion of the carrier member beneath a mattress on which the patient rests, the patient passing through a gap between first and second ends of the carrier member.

6. The method of claim 5, wherein the moving step comprises rotating the carrier member.

7. The method of claim 5, wherein the moving step comprises translating the carrier member.

8. The method of claim 1, wherein the positioning step comprises placing the carrier member around a head of the patient so that the axis is substantially parallel to an ear-to-ear axis of the patient.

9. The method of claim 1, wherein the positioning step comprises placing the carrier member around the head of the patient so that the axis is substantially parallel to an axis extending from a nose of the patient to a back of a head of the patient.

10. An imager for the study of a patient to whom a radionuclide has been administered, comprising:

an arcuate detector carrier member encompassing at least 180 degrees of an arc about an examination axis through a target area of the patient; and one or more detectors which are capable of moving along the detector carrier member for taking a plurality of readings of gamma ray emissions from the radionuclide;

wherein the carrier member is substantially immobile relative to the patient while the plurality of readings are taken.

11. The imager of claim 10, wherein said arc is encompassed by the detector carrier member from a first end through a second end with a gap sufficient to permit the relative ingress and egress of the patient through the gap.

12. The imager of claim 11, wherein the detectors are in a detector head moveable along the carrier member to take said plurality of readings.

13. The imager of claim 12, wherein the detector head is moveable along an arc defined by the carrier member.

14. The imager of claim 12, wherein the detector head is moveable along a non-circular arc defined by the carrier member, the noncircular arc corresponding more nearly to the perimeter of the patient than would a circular arc.

15. The imager of claim 10, wherein the carrier member has a shell, extending substantially along the length of the carrier member for preventing physical contact between the patient or the patient's environment and the detectors, while being substantially gamma transparent so as to allow the detectors to detect radiation passing through the shell.

16. The imager of claim 10, wherein all the detectors are positioned at different fixed locations along the carrier member.

17. The imager of claim 10, wherein the carrier member has first and second substantially flat portions, parallel to each other and joined by a curved portion, the detectors being substantially continuously arrayed along said flat portions and curved portion.

18. The imager of claim 11 further comprising:

a gantry for supporting the carrier member above a floor surface and rotatably coupled to the carrier member for relative rotation about a horizontal axis orthogonal to the examination axis so as to accommodate multiple orientations of the examination axis.

19. The imager of claim 18, wherein the gantry comprises:

a base section for supporting the imager on a floor surface;

a tower section extending upward from the base section; and an arm section coupling the tower section and the carrier member.

20. An imager for the study of a patient, comprising:

an arcuate detector carrier member encompassing an arc about an examination axis through a target area of the patient; and one or more detectors carried at least in part within the detector carrier member for taking a plurality of readings of gamma ray emissions, wherein the one or more detectors moves along the carrier member;

wherein the carrier member is substantially immobile relative to the patient while the plurality of readings are taken.

21. The imager of claim 20 wherein the detector carrier member encompasses less than 360° of arc about the examination axis and wherein the carrier member includes a shell, extending substantially along the length of the carrier member for preventing physical contact between the patient and the one or more detectors.

* * * * *